United States Patent [19]
Su et al.

[11] Patent Number: 6,093,854
[45] Date of Patent: Jul. 25, 2000

[54] PROCESS FOR PREPARING ALKANOLAMINES FROM POLYOLEFIN EPOXIDES

[75] Inventors: Wei-Yang Su; John Michael Larkin, both of Austin, Tex.

[73] Assignee: Huntsman Petrochemical Corporation, Austin, Tex.

[21] Appl. No.: 09/418,686

[22] Filed: Oct. 14, 1999

Related U.S. Application Data

[60] Provisional application No. 60/107,520, Nov. 7, 1998.
[51] Int. Cl.[7] .................................................. C07C 213/00
[52] U.S. Cl. .............................................................. 564/477
[58] Field of Search ............................................... 564/477

[56] References Cited

U.S. PATENT DOCUMENTS

| 4,342,840 | 8/1982 | Kozawa et al. | 521/137 |
|---|---|---|---|
| 4,566,963 | 1/1986 | Ott et al. | 204/181.7 |
| 4,612,335 | 9/1986 | Cuscurida et al. | 521/167 |

*Primary Examiner*—Samuel Barts
*Attorney, Agent, or Firm*—Russell R. Stolle; Ron D. Brown; Christopher J. Whewell

[57] ABSTRACT

Disclosed herein is a process for producing alkanolamines from the reaction between a polyolefin epoxide and an organic amino compound under conditions of elevated temperature and pressure, in the presence of a catalytic amount of an alcohol. Higher reaction rates for alkanolamine production than provided in the prior art may be achieved by use of a process according to the invention. Alkanolamines having various levels of nitrogen may be produced by the invention.

27 Claims, No Drawings

PROCESS FOR PREPARING ALKANOLAMINES FROM POLYOLEFIN EPOXIDES

This Application claims the benefit of U.S. Provisional Application Ser. No. 60/107,520 filed Nov. 7, 1998, which was pending at the time this Application was filed.

This invention relates to a process for producing alkanolamines. More particularly, the invention relates to a process for producing alkanolamines from epoxides by admixture of an epoxide with an amino compound having at least one hydrogen atom attached to a nitrogen atom in the presence of a catalytic amount of an alcohol. Preferably, the epoxide is derived from a polyolefin.

BACKGROUND

Alkanolamines have been known for decades and generally comprise an alcohol function and an amino function as a part of the same organic molecule. Some of the simplest alkanolamines include those known by those in the art familiar with saponification, such as the ethanolamines: mono-, di-, and tri-ethanol amines. The number of higher ethanolamines which are possible is great, as the chain length of the hydrocarbon portion of a given alkanolamine molecule can be varied from about 2 carbon atoms to upwards of hundreds of carbon atoms in the case where the alkanolamine is derived from a polymeric substrate. While it is to the higher alkanolamines to which the present invention is primarily directed; the instant process is applicable to production of the lower alkanolamines as well. However, the benefits conferred through use of the invention are most pronounced in the case of the production of alkanolamines having molecular weights in excess of about 500.

Alkanolamines, or hydroxyalkyl amines as they are sometimes referred to, are useful as additives for motor fuels, including, but not limited to those motor fuels defined by ASTM specification D-439-73, as such amines tend to reduce or eliminate unwanted deposits in the intake manifold, runners, intake valve, and valve bowl area of a conventional automobile engine. Examples of patents describing the use of such materials for this purpose include the international patent application filed under the PCT identifiable as international publication number WO 92/14806 of Ferro Corporation, Cleveland, Ohio, USA, published Sep. 3, 1992, European Patent Specification EP 0 516 838 B1 (International Publication number WO 92/12221), (Chevron Inc.), published Jul. 23, 1992, and European Patent Specification EP 0 476 485 B1, (BASF) published Mar. 25, 1992, the entire contents of all three of which references are herein incorporated by reference thereto. The use of these materials as additives for motor fuels is particularly attractive owing to the fact that they are halogen-free, which means that organic halogen compounds are not formed as a result of their combustion.

One synthetic route by which alkanolamines of high molecular weight may be prepared is the multi-step process wherein a polyolefin is first converted to an epoxide by means known to those skilled in the art. Such means may be effected on any polyolefin, but the polyolefins polyethylene, polypropylene, and polybutylene have been traditionally preferred. Generally, an olefin homo- or co-polymer having a molecular weight in the range of 170 to 5000, preferably 300 to 4000, more preferably 400 to 3500, and most preferably 500 to 3000, is charged to a reactor along with an effective amount of hydrogen peroxide, and especially preferably along with a catalytic amount of a carboxylic acid, which catalyzes the epoxidation of the olefin by presumably forming a peroxy acid as an intermediate. The reaction is carried out at a temperature in the range of about 60 to 85 degrees centigrade, and other conditions for such a reaction is described in Organic Peroxides, Vol. 1, Wiley-Interscience, New York, 1970, Daniel Swern at pages 340–369, inter alia, the entire contents of which are herein incorporated by reference thereto, as well as the patent publications already mentioned. Additionally, it has been found by some workers to be convenient to employ a hydrocarbon solvent in which to carry out the epoxidation. Typically, as is evident from the prior art cited herein, several hours are required to effect a significant degree of reaction between an epoxidized polyolefin and an amino compound, with reaction times on the order of 10 to 16 hours being typical. Through use of the instant invention, the reaction time may be reduced to only 2 to 3 hours. Reaction conditions are described in the prior art herein incorporated by reference.

SUMMARY OF THE INVENTION

It has been unexpectedly discovered that the presence of a catalytic amount of an alcohol greatly accelerates the rate of the reaction between the epoxide and the amino compound in the formation of alkanols therefrom. Accordingly, this invention is an alcohol-catalyzed process for forming an alkanolamine from an epoxide and an amino compound which comprises providing an epoxide and providing an amino compound, and preferably mixing both in a reaction vessel capable of withstanding pressures on the order of 3000 psig and 300 degrees centigrade which is also equipped with a mechanical mixer. An effective catalytic amount of an alcohol is added to the aforesaid mixture of amino compound and epoxide, and either the temperature or pressure, or both are elevated sufficiently to cause a reaction that results in the formation of an alkanolamine.

DETAILED DESCRIPTION

The present invention is a process for preparing alkanolamines by reacting an epoxide, and especially a polyolefin epoxide, with an amino compound. By their invention, the inventors hereof have discovered that the time required for the reaction can be shortened significantly by having a catalytic amount of an alcohol present. In order to form an alkanolamine from an epoxide and an amino compound according to the invention, the process includes charging of an epoxidized polymer to a reactor along with an amino compound. The amino compound and the epoxidized polyolefin are charged to a reactor and subjected to conditions of elevated temperature and pressure which, although the inventors do not wish to be bound by any particular theory, is believed to cause the epoxide ring to open, and wherein the active hydrogen atom from a nitrogen atom is transferred to the oxygen atom of the epoxide to form a nascent hydroxy group on the polymer, and a carbon-nitrogen bond is formed between the nitrogen atom of the amino compound and the carbon atom adjacent to the nascent hydroxy group.

Any amino compound is suitable for the reaction, provided that the amino compound contains at least one hydrogen attached to a nitrogen atom, and that no other functional groups are present in the molecule which would interfere substantially with the formation of the alkanolamine. Suitable amines for the reaction are exemplified by, but not limited to, those mentioned in the aforesaid patent publications, especially the preferred amine compounds mentioned on the bottom of page 14 of PCT publication 92014806. For purposes of this specification and the appended claims the words "amino compound" means ammonia or any organic compound comprising at least one nitrogen atom, wherein the nitrogen atom has at least one hydrogen atom bound thereto, regardless of the aromaticity, chain branching, lack of chain branching, or presence of other known functional groups present in the compound as a whole, including without limitation those mentioned in PCT publication 92014806, and wherein there is at least one nitrogen to carbon bond. It is readily recognized and appreciated by those skilled in the organic chemical arts that included within this definition are all organic mono- and polyamines. These include without limitation ammonia, monoalkylamines, dialkylamines, polyalkylene polyamines, alkylene polyamines, and amino acids. According to the invention, amino compounds suitable for use herein may contain a hydrocarbyl group that is straight-chain, branched, cyclic, un-substituted, or substituted with various substituents known to those skilled in the art as substituents in organic chemistry, with the proviso that a substance, in order to qualify as an amino compound for purposes of this specification and the appended claims must contain at least one active hydrogen atom bonded to a nitrogen atom, and must not contain any other substituents in the molecule which preclude formation of alkanolamine. Suitable substituents include halogens, cyano groups, ester groups, ether linkages, amido, etc. As used herein, the term "hydrocarbyl" means a moiety comprising a carbon atom having at least one hydrogen atom bonded to it, and includes alkyl groups, alkenyl groups, alkynly groups, phenyl groups, benzyl groups aceto groups, as well as other hydrocarbon-bearing species, whether such are straight chain, branched, or cyclic, and saturated or unsaturated.

Exemplary but not delimitive of the class of monoalkylamines are: methylamine, ethylamine, n-propylamine, butylamine, and other higher analogues in this homologous series, (regardless of the presence or absence of chain branching or substitution, i.e., compounds such as 2-aminopropane and 4-aminononane fall within this class) aniline, phenethylamine etc. Exemplary but not delimitive of the class of dialkylamines are diethylamine, dimethylamine, dipropylamine, and other higher analogues in this homologous series including those either with or without chain branching present. Dialkylamines by definition contain at least two hydrocarbyl, (which are commonly alkyl) groups attached to a nitrogen atom. It is believed to be well-known to those skilled in the chemical arts that the two alkyl groups need not necessarily be the same, but may differ. For example, there is a compound known as N-methyl, N-ethyl amine which has both an ethyl and a methyl group bonded to a nitrogen atom, in addition to an active hydrogen atom. Thus the present invention contemplates the use of amino compounds having either the same or different hydrocarbyl groups attached to the same nitrogen atom, wherein one, both, or neither of such hydrocarbyl groups of the dialkylamine include another nitrogen atom bonded to one of its carbon atoms.

Polyalkylene polyamines are also useful in processes carried out in accordance with the principles of this invention, and exemplary but not delimitive of these materials are the amines which contain more than one alkyl group, wherein the alkyl groups are joined together by a nitrogen atom which may or may not have another substituent on the bridging nitrogen atom, with the proviso, as is required of all amines useful in accordance with this invention, that the molecule as a whole must contain at least one nitrogen atom which has an active hydrogen atom bonded to it. Such amines are well known in the art and are exemplified without limitation by diethylene triamine, dipropylene triamine, dibutylene triamine, triethylene tetramine, tripropylene tetramine, tetraethylene pentamine, hexamethylene diamine, hexamethylenetetramine, etc., as members of compounds of polyalkylene polyamines are known to those skilled in the art.

The alkylene polyamines are organic amino compounds which comprise a carbon chain having more than one nitrogen atom bonded to the carbon chain. Exemplary of this class of compounds are 1,3 propanediamine, ethylene diamine, butylamine diamines, etc., including those having at least one other hydrocarbyl group attached to one or more of the nitrogen atoms. Again, the main proviso is that the amino compound contain an active hydrogen atom bonded to a nitrogen atom that is capable of undergoing reaction with an epoxide to form an alkanolamine, as active hydrogen atoms bonded to nitrogen atoms capable of participating in such reactions are well-known to those skilled in the art. Such compounds are exemplified by N,N-dimethylaminopropylamine, which is structurally an n-propyl amine molecule which includes a dimethylamino group bonded to the gamma carbon atom, which may also be termed 1-amino, 3-(N,N-dimethylamino) propane.

For purposes of this specification and the appended claims the word "epoxide" means any epoxide, that is, an organic compound which contains an oxirane ring, which ring is defined as a three-membered ring comprising two carbon atoms and an oxygen atom. Such materials are well-known to be formed from the reaction between a peroxide and an olefin. Exemplary materials of this class are ethylene oxide, propylene oxide, and butylene oxide. These materials are made industrially by the gas phase oxidation of ethylene, propylene, and a butene, respectively. However, alternatively, as already mentioned, olefinic bonds may be epoxidized by a peroxide. The word epoxide includes all materials having an oxirane ring, regardless of their molecular weight. However, the catalytic effect discovered by the inventors hereof is pronounced in the case when the epoxide has a molecular weight in excess of 170, more pronounced when the molecular weight is in excess of 300, and most pronounced when the epoxide has a molecular weight in excess of 500.

Suitable alcohols include any alcohol, straight chain, branched, or cyclic, in which no appreciable amount of polyolefin epoxide is able to dissolve. For purposes of this specification and the appended claims, the term "straight-chain" means alcohols referred to by those of ordinary skill in the art as normal alcohols, while "branched alcohols" are those which possess even the smallest degree of what is well known to those skilled in the art as "chain branching". All alcohols are either straight chain, branched, or cyclic. A suitable alcohol for use in the invention is cyclohexanol. Another preferred alcohol for purposes of this invention is ethanol. The currently most preferred alcohol for this invention is methanol.

An alcohol used as a catalyst according to the process of the invention does not exert any solvent effect on the epoxidized polyolefin, but is present, rather, in a catalytic amount. Alcohols are organic compounds having a hydroxy group attached to a carbon atom, as is well-known to those of ordinary skill in the chemical arts. For purposes of the instant invention, the word alcohol means all such compounds generally recognized as alcohols. The term also includes poly-ols, that is, organic molecules having more than one hydroxy group per molecule. The process herein may be operated in a batch process, or continuously. In a preferred form of the invention, the alcohol catalyst used is not miscible with the polyolefin epoxide employed as a reactant. For purposes of this invention and the appended claims, the word "insoluble" means that the solute material is soluble to less than 10 grams per liter in the solvent material.

It will be readily appreciated by those skilled in the art that materials having various levels of nitrogen content, as expressed on a weight percent basis, may be produced in accordance with the invention. This is due to the versatility of the process in that a wide variety of possible polyolefin epoxides may be reacted with a wide variety of possible amino compounds. When a polyolefin epoxide having relatively low molecular weight is reacted with an amino compound having a high percentage of nitrogen, high levels of nitrogen in the finished product are encountered. For example, when hexamethylene heptamine (M.W.=c.a.271) is reacted with a polyolefin epoxide having a molecular weight of about 500, the resulting product has a molecular weight of about 770, and is about 12.7% nitrogen. Therefore, by judicious choice of reactants, one of ordinary skill after reading this specification and claims may produce alkanolamines having nitrogen contents between about 0.03% by weight and 20.0+%. Preferably, when the products are to be used as additives for motor fuels, the reactants are selected to provide a product having between about 0.10% and 10% nitrogen by weight, including every hundredth percentage therebetween. More preferably, the nitrogen content is between 0.20% and 5.0%, and it is most preferred that the nitrogen content be about 3.0% when the product is to be admixed with gasoline for use as a motor fuel, to facilitate blending. However, these ranges and percents should be viewed as exemplary of the invention and not as delimitive thereof, as the artisan of ordinary skill may readily determine the reactants necessary to provide a desired nitrogen content in the finished product.

It is preferable to carry out reactions undertaken in accordance with this invention at conditions of elevated temperature and pressure. For purposes of this specification and the appended claims, the words "elevated temperature and pressure" mean either a condition of elevated temperature, or a condition of elevated pressure, or, as is most preferred, a combination of the two. "Elevated" with respect to temperature means any degree of temperature greater than 20 degrees centigrade. "Elevated" with respect to pressure means any pressure greater than atmospheric pressure. Conditions of elevated temperature may be used independently of one another, or simultaneously, at any level or degree of either independent of one another. Most preferably, the temperature is 200 degrees Centigrade, and most preferably, the pressure is 1800 psig.

The following are examples of reactions conducted in accordance with the invention and should be considered by all readers hereof as being merely exemplary of the invention, and not delimitive of it in any way.

EXAMPLE I

A one-liter stirring autoclave is charged with 400 grams of a polyolefin epoxide having a molecular weight of about 1000 and 24 grams of methanol. The reactor is sealed from the atmosphere and purged with gaseous nitrogen prior to charging with 150 grams of anhydrous ammonia. The reactor is heated to a temperature of 200 degrees centigrade for three hours after which time the reactor is cooled to ambient temperature and vented. The resultant product is transferred to a flask and subsequently subjected to reduced pressure, under moderate stirring, to remove traces of methanol and ammonia in the mass. Following removal of such light-boiling fractions, the product is analyzed and found to contain 0.56% nitrogen.

EXAMPLE II

Continuous Process

A 200 cc DOWTHERM® heated, stainless steel tubular upflow reactor which has an inside diameter of 0.815" and a thermowell fabricated from ¼-inch 0. D. tubing extended upward into the reactor and equipped with a baffle is used. A polyolefin epoxide of molecular weight of about 1000 is fed at a rate of 120 grams per hour through the tube along with a mixture of ammonia and methanol (at a weight ratio of $NH_3$:MeOH of 9 to 1, respectively) also fed at a rate of 120 grams per hour. The tube reactor is maintained at a temperature of 220 degrees centigrade at a pressure of 2200 psig. The reactor effluent is stripped of ammonia, methanol, and other light materials by means known to those in the art to produce a material which contains 0.13% nitrogen.

EXAMPLE III

The procedure of Example II is followed except that the epoxide is fed at a rate of 40 grams per hour and the mixture of ammonia to methanol had a ratio of 3 to 2 and is fed at a rate of 50 grams per hour. The resulting product contained 0.63% nitrogen.

EXAMPLE IV

The procedure of Example II is followed except that the epoxide is fed at about 40 grams per hour and a mixture of ethylene diamine and methanol at a weight ratio of 3 to 2 is fed at about 50 grams per hour. The reaction is conducted at 230 degrees centigrade and 2000 psig. The reactor effluent is dissolved in xylene and washed with water. Xylene and other lights are removed under reduced pressure. The resulting product is analyzed to contain about 1.81% nitrogen.

EXAMPLE V

The procedure of Example IV is followed, with the exception that N,N-dimethyl aminopropylamine is used in the stead of ethylenediamine. The lights are removed from the reactor effluent by distillation. The resulting product is analyzed to contain about 1.65% nitrogen.

Although the present invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims which now follow.

We claim:

1. An alcohol-catalyzed process for forming an alkanolamine from an epoxide and an amino compound which comprises:
   a) providing an epoxide;
   b) providing an amino compound;
   c) providing an effective catalytic amount of an alcohol;
   d) causing the amino compound to contact the epoxide in the presence of said catalytic amount of an alcohol under conditions of elevated temperature and pressure sufficient to cause a reaction resulting in the formation of an alkanolamine.

2. The process according to claim 1 wherein said conditions include elevation of the temperature at which the reaction takes place to a temperature in the range of about 50 degrees centigrade to 300 degrees centigrade, including every degree therebetween.

3. The process according to claim 1 wherein said conditions include elevation of the temperature at which the reaction takes place to a temperature in the range of about 150 degrees centigrade to 250 degrees centigrade, including every degree therebetween.

4. The process according to claim 1 wherein said conditions include elevation of the temperature at which the reaction takes place to a temperature in the range of 180 degrees centigrade to 230 degrees centigrade, including every degree therebetween.

5. The process according to claim 1 wherein said epoxide is an epoxide of a polyolefin.

6. The process according to claim 1 wherein said polyolefin is derived from an olefinic monomer having a carbon atom content of between one and twelve carbon atoms per molecule, including every integral number of carbon atoms therebetween, and whether straight-chain, branched, or cyclic.

7. The process according to claim 5 wherein said epoxide has a molecular weight in the range of 170 to 5000 and every molecular weight therebetween.

8. The process according to claim 5 wherein said epoxide has a molecular weight in the range of 500 to 2500, and every molecular weight therebetween.

9. The process according to claim 5 wherein said epoxide has a molecular weight in the range of 750 to 1800 and every molecular weight therebetween.

10. The process according to claim 1 wherein said alcohol has fewer than ten (10) carbon atoms per molecule, and said epoxide is insoluble in said alcohol.

11. The process according to claim 1 wherein the pressure is in the range of: atmospheric pressure to 5000 psig, including every integer psig therebetween.

12. The process according to claim 1 wherein the pressure is in the range of: 1000 to 3000 psig and every degree of psig therebetween.

13. The process according to claim 1 wherein the pressure is in the range of 1500 to 2500 psig and every degree of psig therebetween.

14. The process according to claim 1 wherein said alcohol is selected from alcohols having between 1 and 20 carbon atoms per molecule.

15. The process according to claim 1 wherein said alcohol is selected from alcohols having between 1 and 10 carbon atoms per molecule.

16. The process according to claim 14 wherein said alcohol is a straight chain alcohol.

17. The process according to claim 14 wherein said alcohol is a branched alcohol.

18. The process according to claim 15 wherein said alcohol is selected from the group consisting of: methanol, ethanol, n-propanol, 2-propanol, n-butanol, 2-butanol, and sec-butanol.

19. The process according to claim 1 wherein the amino compound contains at least one hydrogen atom bonded to a nitrogen atom.

20. The process according to claim 1 wherein the amino compound is selected from the group consisting of: ammonia, monoalkylamines, dialkylamines, polyalkylene polyamines, alkylene polyamines, and amino acids.

21. The process according to claim 1 wherein said process is conducted in a batch fashion.

22. The process according to claim 1 wherein said process is conducted in a continuous fashion.

23. The process according to claim 22 wherein said process is conducted in a tubular reactor.

24. The process of claim 1 wherein said contact includes mechanical mixing.

25. In a process for producing an alkanolamine by reaction of a polyolefin epoxide with an amino compound by contacting a polyolefin epoxide with an amino compound at an elevated temperature and pressure, wherein the improvement comprises carrying out the reaction in the presence of a catalytic amount of an alcohol.

26. A process according to claim 25 wherein the reactants are selected to provide a nitrogen content in the alkanolamine product of between 0.03% by weight and 20% by weight, including every hundredth percentage therebetween.

27. A process according to claim 25 wherein the reactants are selected to provide a nitrogen content in the alkanolamine product of between 0.20% by weight and 3.0% by weight.

* * * * *